(12) United States Patent
Sandelson et al.

(10) Patent No.: US 12,295,683 B2
(45) Date of Patent: May 13, 2025

(54) SYSTEMS AND METHODS FOR ROBOTIC COLLISION AVOIDANCE USING MEDICAL IMAGING

(71) Applicant: Mazor Robotics Ltd., Caesarea (IL)

(72) Inventors: Adi Sandelson, Givatayim (IL); Nimrod Dori, Atlit (IL)

(73) Assignee: Mazor Robotics Ltd., Caesarea (IL)

( * ) Notice: Subject to any disclaimer, the term of this patent is extended or adjusted under 35 U.S.C. 154(b) by 387 days.

(21) Appl. No.: 17/590,891

(22) Filed: Feb. 2, 2022

(65) Prior Publication Data

US 2023/0240774 A1     Aug. 3, 2023

(51) Int. Cl.
   *A61B 34/32*     (2016.01)

(52) U.S. Cl.
   CPC .................................. *A61B 34/32* (2016.02)

(58) Field of Classification Search
   None
   See application file for complete search history.

(56) References Cited

U.S. PATENT DOCUMENTS

| | | | |
|---|---|---|---|
| 11,633,246 B2 * | 4/2023 | Cavalier | A61B 34/37 606/130 |
| 2016/0015473 A1 | 1/2016 | Frimer et al. | |
| 2017/0202624 A1 * | 7/2017 | Atarot | G16H 40/63 |
| 2020/0035348 A1 * | 1/2020 | Sartor | A61B 90/361 |
| 2020/0078097 A1 | 3/2020 | Gregerson et al. | |
| 2020/0335207 A1 | 10/2020 | Kara et al. | |

FOREIGN PATENT DOCUMENTS

| WO | WO 2016/187290 | 11/2016 |
|---|---|---|
| WO | WO 2018/076114 | 5/2018 |
| WO | WO 2020/153411 | 7/2020 |
| WO | WO 2020/236937 | 11/2020 |
| WO | WO 2021/062373 | 4/2021 |
| WO | WO 2021/125115 | 6/2021 |
| WO | WO 2021/195369 | 9/2021 |

OTHER PUBLICATIONS

International Search Report and Written Opinion for International (PCT) Patent Application No. PCT/IL2023/050062, dated Apr. 14, 2023, 16 pages.

\* cited by examiner

*Primary Examiner* — Kyle T Johnson
*Assistant Examiner* — Arslan Azhar
(74) *Attorney, Agent, or Firm* — Sheridan Ross P.C.

(57) ABSTRACT

Systems and methods according to embodiments of the present disclosure include: receiving registration data including information about a location of an anatomical element in a surgical environment; defining, based on the registration data, a three-dimensional (3D) volume in the surgical environment including the anatomical element; and controlling a robotic arm inside the surgical environment based on the defined 3D volume such that at least the robotic arm or one or more components attached to the robotic arm avoids passing through the defined 3D volume during a movement of the robotic arm.

20 Claims, 5 Drawing Sheets

SYSTEMS AND METHODS FOR ROBOTIC COLLISION AVOIDANCE USING MEDICAL IMAGING

BACKGROUND

The present disclosure is generally directed to surgical navigation, and relates more particularly to navigation of surgical robots.

Surgical robots may assist a surgeon or other medical provider in carrying out a surgical procedure, or may complete one or more surgical procedures autonomously. Imaging may be used by a medical provider for diagnostic and/or therapeutic purposes. Patient anatomy can change over time, particularly following placement of a medical implant in the patient anatomy.

BRIEF SUMMARY

Example aspects of the present disclosure include:

A method according to at least one embodiment of the present disclosure comprises: receiving registration data including information about a location of an anatomical element in a surgical environment; defining, based on the registration data, a three-dimensional (3D) volume in the surgical environment including the anatomical element; and controlling a robotic arm inside the surgical environment based on the defined 3D volume such that at least the robotic arm or one or more components attached to the robotic arm avoids passing through the defined 3D volume during a movement of the robotic arm.

Any of the aspects herein, wherein the registration data includes information from one or more of a Computed Tomography (CT) image, a Magnetic Resonance Image (MM), and a fluoroscopic image.

Any of the aspects herein, further comprising: registering the defined 3D volume to the robotic arm.

Any of the aspects herein, wherein the anatomical element comprises at least one of a vertebra, a hard tissue, a soft tissue, an artery, or a nerve.

Any of the aspects herein, further comprising: controlling a second robotic arm based on the defined 3D volume, wherein at least one of the second robotic arm or components attached to the second robotic arm passes through the defined 3D volume.

Any of the aspects herein, further comprising: determining, based on the defined 3D volume, a first navigation path of the robotic arm; and determining, based on at least one of the defined 3D volume or the first navigation path, a second navigation path of the second robotic arm.

Any of the aspects herein, wherein the controlling of the second robotic arm further comprises: restricting, when the second robotic arm passes through the defined 3D volume, the movement of the robotic arm.

Any of the aspects herein, wherein the one or more components of the robotic arm comprises at least one of a surgical drill, a surgical saw, a surgical scalpel, a surgical reamer, a surgical tap, an ultrasonic blade, a surgical burr, a surgical screw, or an interbody element.

A system according to at least one embodiment of the present disclosure comprises: a processor; and a memory storing data thereon that, when executed by the processor, cause the processor to: receive registration data including information about a location of an anatomical element in a surgical environment; define, based on the registration data, a first three-dimensional (3D) volume in a surgical environment comprising a first portion of the anatomical element; define, based on the registration data, a second 3D volume different from the first 3D volume in the surgical environment comprising a second portion of the anatomical element; and control a robotic arm inside the surgical environment based on the first 3D volume such that at least one of the robotic arm or one or more components attached to the robotic arm avoids passing through the first 3D volume during a movement of the robotic arm.

Any of the aspects herein, wherein the first 3D volume at least partially overlaps the second 3D volume.

Any of the aspects herein, wherein the robotic arm is controlled to pass through the second 3D volume.

Any of the aspects herein, wherein the robotic arm comprises an end effector, and wherein the end effector is controlled to pass through a third 3D volume proximate at least one of the first 3D volume and the second 3D volume.

Any of the aspects herein, wherein the first 3D volume and the second 3D volume are mutually exclusive.

Any of the aspects herein, wherein an end effector is mechanically coupled to a first surgical tool, and wherein the first surgical tool comprises a drill, a reamer, a scalpel, a saw, a tap, an ultrasonic blade, a surgical burr, a surgical screw, or an interbody element.

Any of the aspects herein, wherein the data further cause the processor to: define a third 3D volume that abuts at least one of the first 3D volume and the second 3D volume; and control the movement of the robotic arm based on the third 3D volume.

Any of the aspects herein, wherein the registration data includes information from one or more of a Computed Tomography (CT) image, a Magnetic Resonance Image (MM), and a fluoroscopic image.

An apparatus according to at least one embodiment of the present disclosure comprises: a robotic arm that includes an end effector; a processor; and a memory storing data thereon that, when executed by the processor, cause the processor to: receive registration data including information about a location of an anatomical element in a surgical environment; define, based on the registration data, a first three-dimensional (3D) volume in a surgical environment comprising the anatomical element; and maneuver the robotic arm inside the surgical environment based on the first 3D volume such that at the end effector of the robotic arm avoids passing into the first 3D volume.

Any of the aspects herein, wherein the data further cause the processor to: receive one or more intraoperative images; determine, based on the one or more intraoperative images, a second location of the anatomical element in the surgical environment; and change, based on the one or more intraoperative images, the first 3D volume to a second 3D volume.

Any of the aspects herein, wherein the second 3D volume has a volume that is different than the first 3D volume.

Any of the aspects herein, wherein the registration data include a third location of a second anatomical element, and wherein the data further cause the processor to: define a third 3D volume including a portion of the second anatomical element; and maneuver the robotic arm based on the third 3D volume.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/embodiments in combination with any one or more other aspects/features/embodiments.

Use of any one or more of the aspects or features as disclosed herein.

It is to be appreciated that any feature described herein can be claimed in combination with any other feature(s) as described herein, regardless of whether the features come from the same described embodiment.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as X1-Xn, Y1-Ym, and Z1-Zo, the phrase is intended to refer to a single element selected from X, Y, and Z, a combination of elements selected from the same class (e.g., X1 and X2) as well as a combination of elements selected from two or more classes (e.g., Y1 and Zo).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present disclosure will become apparent to those skilled in the art upon consideration of the embodiment descriptions provided hereinbelow.

BRIEF DESCRIPTION OF THE SEVERAL VIEWS OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Alternatively or additionally, functions may be implemented using machine learning models, neural networks, artificial neural networks, or combinations thereof (alone or in combination with instructions). Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), graphics processing units (e.g., Nvidia GeForce RTX 2000-series processors, Nvidia GeForce RTX 3000-series processors, AMD Radeon RX 5000-series processors, AMD Radeon RX 6000-series processors, or any other graphics processing units), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

The terms proximal and distal are used in this disclosure with their conventional medical meanings, proximal being closer to the operator or user of the system, and further from the region of surgical interest in or on the patient, and distal being closer to the region of surgical interest in or on the patient, and further from the operator or user of the system.

One risk associated with utilizing autonomous or semi-autonomous surgical robots is the surgical robot unintentionally colliding with patient anatomy. In at least one embodiment of the present disclosure, medical images taken during the surgical procedure may be utilized to map the anatomical objects (e.g., vertebrae) that the surgical robot must not collide with during movement of the surgical robot.

During robotic-assisted surgery, the robot is registered to the anatomy of the patient (e.g., to vertebrae of the patient), enabling the system to know the location of the robot relative to anatomy (and vice versa) as long as the registration is not lost. Embodiments of the present disclosure may utilize the registration data to execute the robotic tasks. Further, embodiments of the present disclosure may use the position of the anatomy in relation to the surgical robot to build one or more three-dimensional (3D) volumes using the original registration data that was built from medical images (e.g., Computed Tomography (CT) scans, Magnetic Resonance Images (MRI), two-dimensional (2D) X-rays, fluoroscopic images, etc.). The 3D volume portrays the objects through which the robotic arm cannot move or with which the robotic arm cannot collide. Once constructed, the 3D volumes may be factored into every motion calculation for the surgical robot.

In some embodiments, the medical images may be used to build a 3D volume that can be used to map where in space the surgical robot cannot move in, near, and/or through. The medical images can be used as standalone information to create the 3D volume and, additionally, may be combined with other types of data. Non-limiting examples of the other types of data may include a 3D scan, Infrared (IR) Navigation, Optical Navigation, and/or Magnetic Navigation.

Embodiments of the present disclosure may be utilized with any robotic-assisted surgery that implements medical image, as well as any medical scanner that may have automatic movement capability of any component thereof (e.g., an imaging source and/or imaging detector).

Embodiments of the present disclosure provide technical solutions to problems associated with surgical tool or robots unintentionally contacting patient anatomy.

Figure 1:
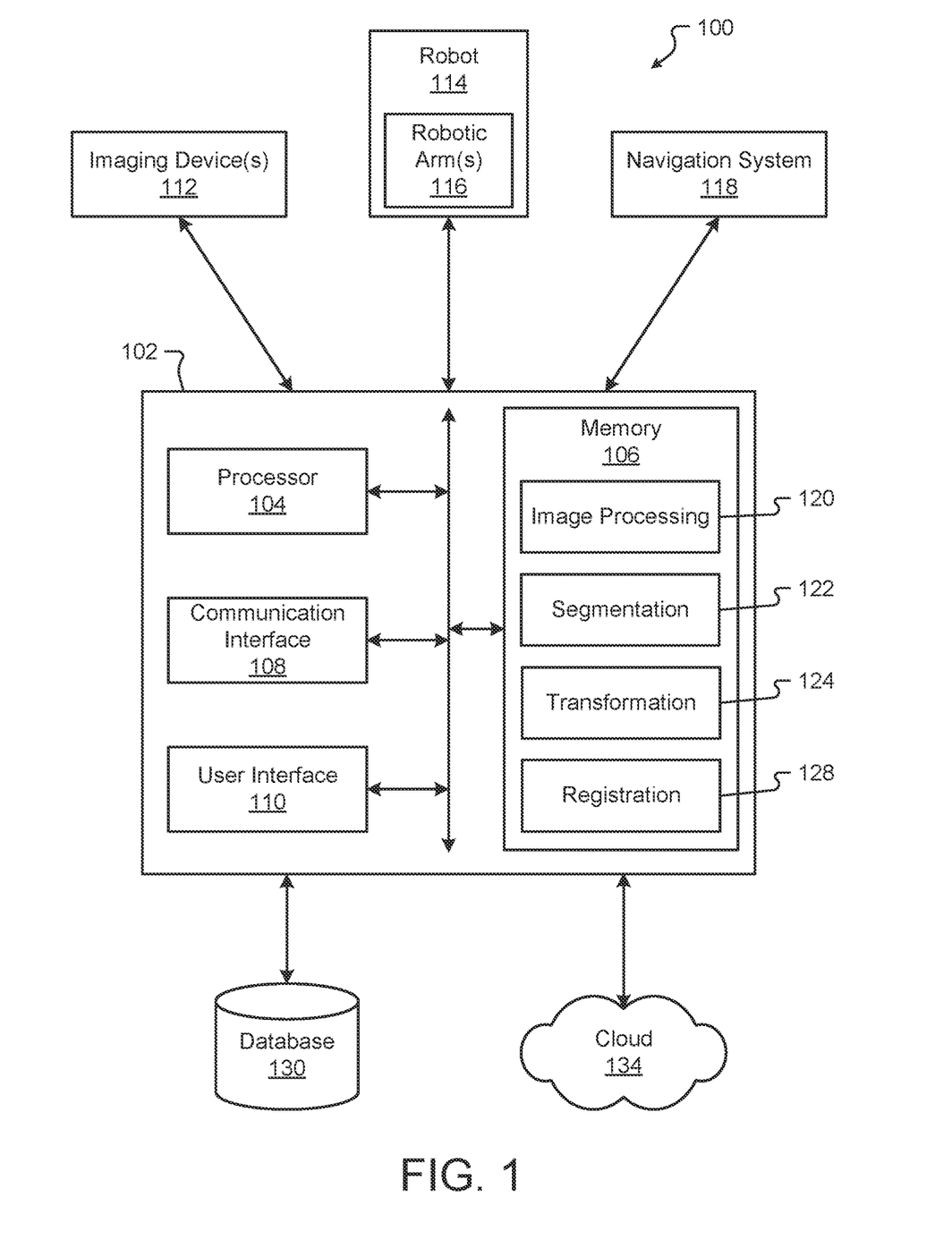
FIG. 1 is a block diagram of aspects of a system according to at least one embodiment of the present disclosure.

Turning first to FIG. 1, a block diagram of a system 100 according to at least one embodiment of the present disclosure is shown. The system 100 may be used to register a surgical robot to one or more anatomical elements; to define one or more 3D volumes around the one or more anatomical elements; to control, pose, and/or otherwise manipulate a surgical mount system, a surgical arm, and/or surgical tools attached thereto based on the one or more 3D volumes; and/or to carry out one or more other aspects of one or more of the methods disclosed herein. The system 100 comprises a computing device 102, one or more imaging devices 112, a robot 114, a navigation system 118, a database 130, and/or a cloud or other network 134. Systems according to other embodiments of the present disclosure may comprise more or fewer components than the system 100. For example, the system 100 may not include the imaging device 112, the robot 114, the navigation system 118, one or more components of the computing device 102, the database 130, and/or the cloud 134.

The computing device 102 comprises a processor 104, a memory 106, a communication interface 108, and a user interface 110. Computing devices according to other embodiments of the present disclosure may comprise more or fewer components than the computing device 102.

The processor 104 of the computing device 102 may be any processor described herein or any similar processor. The processor 104 may be configured to execute instructions stored in the memory 106, which instructions may cause the processor 104 to carry out one or more computing steps utilizing or based on data received from the imaging device 112, the robot 114, the navigation system 118, the database 130, and/or the cloud 134.

The memory 106 may be or comprise RAM, DRAM, SDRAM, other solid-state memory, any memory described herein, or any other tangible, non-transitory memory for storing computer-readable data and/or instructions. The memory 106 may store information or data useful for completing, for example, any step of the methods 300 and/or 400 described herein, or of any other methods. The memory 106 may store, for example, instructions and/or machine learning models that support one or more functions of the robot 114, or that otherwise support and/or enable one or more steps of one or more methods discussed herein. For instance, the memory 106 may store content (e.g., instructions and/or machine learning models) that, when executed by the processor 104, enable image processing 120, segmentation 122, transformation 124, and/or registration 128. Such content, if provided as in instruction, may, in some embodiments, be organized into one or more applications, modules, packages, layers, or engines. Alternatively or additionally, the memory 106 may store other types of content or data (e.g., machine learning models, artificial neural networks, deep neural networks, etc.) that can be processed by the processor 104 to carry out the various method and features described herein. Thus, although various contents of memory 106 may be described as instructions, it should be appreciated that functionality described herein can be achieved through use of instructions, algorithms, and/or machine learning models. The data, algorithms, and/or instructions may cause the processor 104 to manipulate data stored in the memory 106 and/or received from or via the imaging device 112, the robot 114, the database 130, and/or the cloud 134.

The computing device 102 may also comprise a communication interface 108. The communication interface 108 may be used for receiving image data or other information from an external source (such as the imaging device 112, the robot 114, the navigation system 118, the database 130, the cloud 134, and/or any other system or component not part of the system 100), and/or for transmitting instructions, images, or other information to an external system or device (e.g., another computing device 102, the imaging device 112, the robot 114, the navigation system 118, the database 130, the cloud 134, and/or any other system or component not part of the system 100). The communication interface 108 may comprise one or more wired interfaces (e.g., a USB port, an Ethernet port, a Firewire port) and/or one or more wireless transceivers or interfaces (configured, for example, to transmit and/or receive information via one or more wireless communication protocols such as 802.11a/b/g/n, Bluetooth, NFC, ZigBee, and so forth). In some embodiments, the communication interface 108 may be useful for enabling the computing device 102 to communicate with one or more other processors 104 or computing devices 102, whether to reduce the time needed to accomplish a computing-intensive task or for any other reason.

The computing device 102 may also comprise one or more user interfaces 110. The user interface 110 may be or comprise a keyboard, mouse, trackball, monitor, television, screen, touchscreen, and/or any other device for receiving information from a user and/or for providing information to a user. The user interface 110 may be used, for example, to receive a user selection or other user input regarding any step of any method described herein. Notwithstanding the foregoing, any required input for any step of any method described herein may be generated automatically by the system 100 (e.g., by the processor 104 or another component of the system 100) or received by the system 100 from a source external to the system 100. In some embodiments, the user interface 110 may be useful to allow a surgeon or other user to modify instructions to be executed by the processor 104 according to one or more embodiments of the present disclosure, and/or to modify or adjust a setting of other information displayed on the user interface 110 or corresponding thereto.

Although the user interface 110 is shown as part of the computing device 102, in some embodiments, the computing device 102 may utilize a user interface 110 that is housed separately from one or more remaining components of the computing device 102. In some embodiments, the user interface 110 may be located proximate one or more other components of the computing device 102, while in other embodiments, the user interface 110 may be located remotely from one or more other components of the computing device 102.

The imaging device 112 may be operable to image anatomical feature(s) (e.g., a bone, veins, soft tissues, etc.) and/or other aspects of patient anatomy to yield image data (e.g., image data depicting or corresponding to a bone, veins, tissue, etc.). "Image data" as used herein refers to the data generated or captured by an imaging device 112, including in a machine-readable form, a graphical/visual form, and in any other form. In various examples, the image data may comprise data corresponding to an anatomical feature of a patient, or to a portion thereof. The image data may be or comprise a preoperative image, an intraoperative image, a postoperative image, or an image taken independently of any surgical procedure. In some embodiments, a first imaging device 112 may be used to obtain first image data (e.g., a first image) at a first time, and a second imaging device 112 may be used to obtain second image data (e.g., a second image) at a second time after the first time. The imaging device 112 may be capable of taking a 2D image or a 3D image to yield the image data. The imaging device 112 may be or comprise, for example, an ultrasound scanner (which may comprise, for example, a physically separate transducer and receiver, or a single ultrasound transceiver), an O-arm, a C-arm, a G-arm, or any other device utilizing X-ray-based imaging (e.g., a fluoroscope, a CT scanner, or other X-ray machine), a magnetic resonance imaging (MM) scanner, an optical coherence tomography (OCT) scanner, an endoscope, a microscope, an optical camera, a thermographic camera (e.g., an infrared camera), a radar system (which may comprise, for example, a transmitter, a receiver, a processor, and one or more antennae), or any other imaging device 112 suitable for obtaining images of an anatomical feature of a patient. The imaging device 112 may be contained entirely within a single housing, or may comprise a transmitter/emitter and a receiver/detector that are in separate housings or are otherwise physically separated.

In some embodiments, the imaging device 112 may comprise more than one imaging device 112. For example, a first imaging device may provide first image data and/or a first image, and a second imaging device may provide second image data and/or a second image. In still other embodiments, the same imaging device may be used to provide both the first image data and the second image data, and/or any other image data described herein. The imaging device 112 may be operable to generate a stream of image data. For example, the imaging device 112 may be configured to operate with an open shutter, or with a shutter that continuously alternates between open and shut so as to capture successive images. For purposes of the present disclosure, unless specified otherwise, image data may be considered to be continuous and/or provided as an image data stream if the image data represents two or more frames per second.

The robot 114 may be any surgical robot or surgical robotic system. The robot 114 may be or comprise, for example, the Mazor X™ Stealth Edition robotic guidance system. The robot 114 may be configured to position the imaging device 112 at one or more precise position(s) and orientation(s), and/or to return the imaging device 112 to the same position(s) and orientation(s) at a later point in time. The robot 114 may additionally or alternatively be configured to manipulate a surgical tool (whether based on guidance from the navigation system 118 or not) to accomplish or to assist with a surgical task. In some embodiments, the robot 114 may be configured to hold and/or manipulate an anatomical element during or in connection with a surgical procedure. The robot 114 may comprise one or more robotic arms 116. In some embodiments, the robotic arm 116 may comprise a first robotic arm and a second robotic arm, though the robot 114 may comprise more than two robotic arms. In some embodiments, one or more of the robotic arms 116 may be used to hold and/or maneuver the imaging device 112. In embodiments where the imaging device 112 comprises two or more physically separate components (e.g., a transmitter and receiver), one robotic arm 116 may hold one such component, and another robotic arm 116 may hold another such component. Each robotic arm 116 may be positionable independently of the other robotic arm. The robotic arms 116 may be controlled in a single, shared coordinate space, or in separate coordinate spaces.

The robot 114, together with the robotic arm 116, may have, for example, one, two, three, four, five, six, seven, or more degrees of freedom. Further, the robotic arm 116 may be positioned or positionable in any pose, plane, and/or focal point. The pose includes a position and an orientation. As a result, an imaging device 112, surgical tool, or other object held by the robot 114 (or, more specifically, by the robotic arm 116) may be precisely positionable in one or more needed and specific positions and orientations.

The robotic arm(s) 116 may comprise one or more sensors that enable the processor 104 (or a processor of the robot 114) to determine a precise pose in space of the robotic arm (as well as any object or element held by or secured to the robotic arm).

In some embodiments, reference markers (e.g., navigation markers) may be placed on the robot 114 (including, e.g., on the robotic arm 116), the imaging device 112, or any other object in the surgical space. The reference markers may be tracked by the navigation system 118, and the results of the tracking may be used by the robot 114 and/or by an operator of the system 100 or any component thereof. In some embodiments, the navigation system 118 can be used to track other components of the system (e.g., imaging device 112) and the system can operate without the use of the robot 114 (e.g., with the surgeon manually manipulating the imaging device 112 and/or one or more surgical tools, based on information and/or instructions generated by the navigation system 118, for example).

The navigation system 118 may provide navigation for a surgeon and/or a surgical robot during an operation. The navigation system 118 may be any now-known or future-developed navigation system, including, for example, the Medtronic StealthStation™ S8 surgical navigation system or any successor thereof. The navigation system 118 may include one or more cameras or other sensor(s) for tracking one or more reference markers, navigated trackers, or other objects within the operating room or other room in which some or all of the system 100 is located. The one or more cameras may be optical cameras, infrared cameras, or other cameras. In some embodiments, the navigation system 118 may comprise one or more electromagnetic sensors. In various embodiments, the navigation system 118 may be used to track a position and orientation (e.g., a pose) of the imaging device 112, the robot 114 and/or robotic arm 116, and/or one or more surgical tools (or, more particularly, to track a pose of a navigated tracker attached, directly or indirectly, in fixed relation to the one or more of the foregoing). The navigation system 118 may include a display for displaying one or more images from an external source (e.g., the computing device 102, imaging device 112, or other source) or for displaying an image and/or video stream from the one or more cameras or other sensors of the navigation system 118. In some embodiments, the system 100 can operate without the use of the navigation system 118. The navigation system 118 may be configured to provide guidance to a surgeon or other user of the system 100 or a component thereof, to the robot 114, or to any other element of the system 100 regarding, for example, a pose of one or more anatomical elements, whether or not a tool is in the proper trajectory, and/or how to move a tool into the proper trajectory to carry out a surgical task according to a preoperative or other surgical plan.

The database 130 may store information that correlates one coordinate system to another (e.g., one or more robotic coordinate systems to a patient coordinate system and/or to a navigation coordinate system). The database 130 may additionally or alternatively store, for example, one or more surgical plans (including, for example, pose information about a target and/or image information about a patient's anatomy at and/or proximate the surgical site, for use by the robot 114, the navigation system 118, and/or a user of the computing device 102 or of the system 100); one or more images useful in connection with a surgery to be completed by or with the assistance of one or more other components of the system 100; and/or any other useful information. The database 130 may be configured to provide any such information to the computing device 102 or to any other device of the system 100 or external to the system 100, whether directly or via the cloud 134. In some embodiments, the database 130 may be or comprise part of a hospital image storage system, such as a picture archiving and communication system (PACS), a health information system (HIS), and/or another system for collecting, storing, managing, and/or transmitting electronic medical records including image data.

The cloud 134 may be or represent the Internet or any other wide area network. The computing device 102 may be connected to the cloud 134 via the communication interface 108, using a wired connection, a wireless connection, or both. In some embodiments, the computing device 102 may communicate with the database 130 and/or an external device (e.g., a computing device) via the cloud 134.

The system 100 or similar systems may be used, for example, to carry out one or more aspects of any of the methods 300 and/or 400 described herein. The system 100 or similar systems may also be used for other purposes.

Figure 2A:
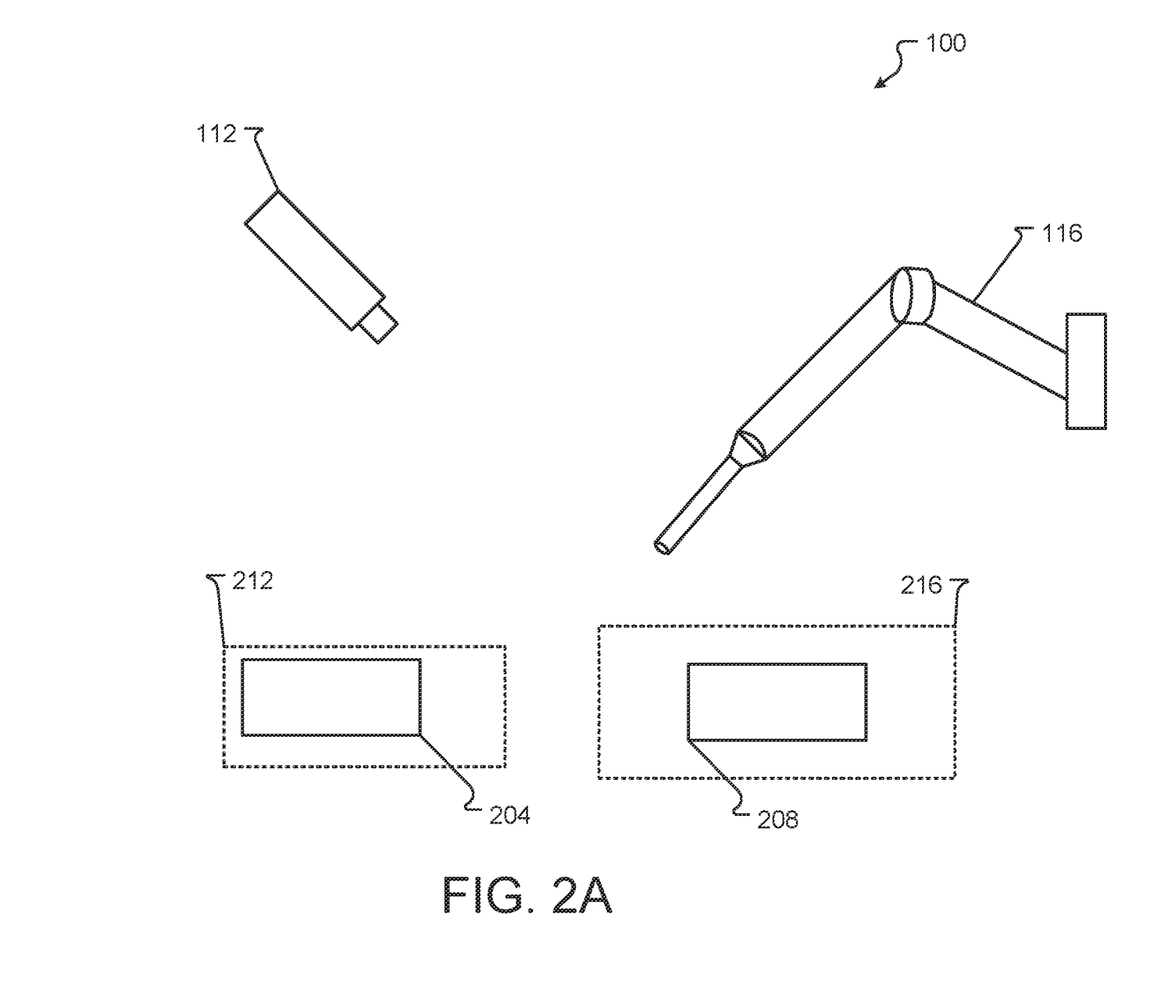
FIG. 2A is a block diagram of aspects of the system according to at least one embodiment of the present disclosure.
Figure 2B:
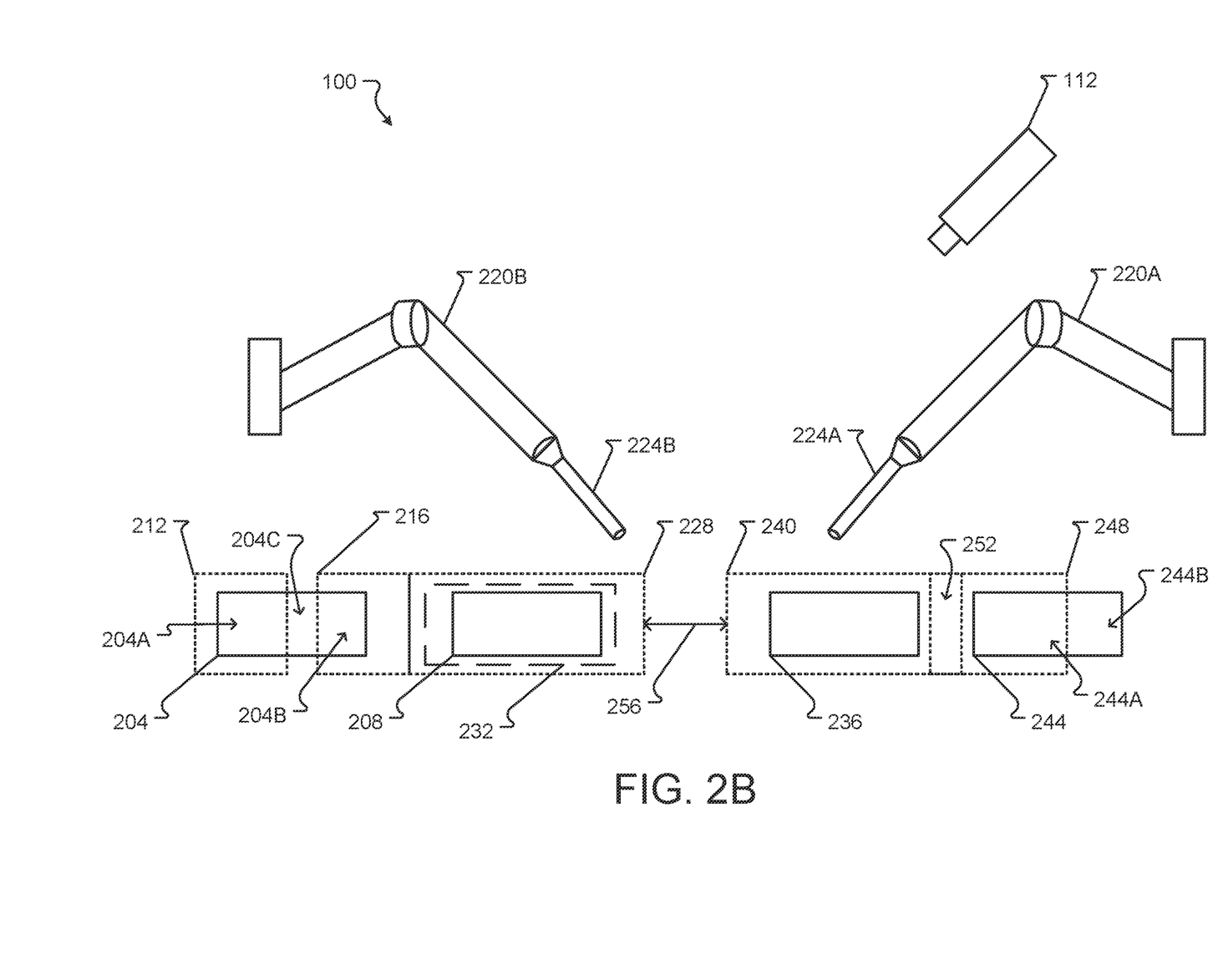
FIG. 2B is a block diagram of aspects of the system according to at least one embodiment of the present disclosure.

Turning next to FIGS. 2A-2B, aspects of the system 100 are shown according to at least one embodiment of the present disclosure. The aspects include an imaging device 112, a robotic arm 116, a first anatomical element 204, and a second anatomical element 208.

The first anatomical element 204 and/or the second anatomical element 208 may be or comprise patient anatomy (e.g., vertebrae) upon which a surgery or surgical procedure is being performed. For instance, the first anatomical element 204 and the second anatomical element 208 may both be vertebrae subject to a spinal fusion. In other embodiments, the first anatomical element 204 may be a vertebra that is the subject of the surgery or surgical procedure, while the second anatomical element 208 is a vertebra that is not subject to the surgery or surgical procedure (or vice versa).

The first anatomical element 204 may include a first 3D volume 212 and the second anatomical element 208 may include a second 3D volume 216. The first 3D volume 212 and/or the second 3D volume 216 may be defined by the computing device 102, the processor 104, or another component of the system 100 based on, for example, one or more preoperative images (e.g., captured by the imaging devices 112), one or more intraoperative images (e.g., captured by the imaging devices 112), image information retrieved from the database 130, combinations thereof, and/or the like. In some embodiments, the 3D volumes 212, 216 may be centered around the anatomical elements 204, 208 (as depicted by the second anatomical element 208 and the second 3D volume 216 in FIG. 2A), while in other embodiments the 3D volumes 212, 216 may not be centered the anatomical element (as depicted by the first anatomical element 204 and the first 3D volume 212 in FIG. 2A).

In some embodiments, the first 3D volume 212 and/or the second 3D volume 216 may be volumes through which and/or near to which the robotic arm 116 cannot move. In other embodiments, the first 3D volume 212 and/or the second 3D volume 216 may be entered by the robotic arm 116, subject to certain constraints on the movement of the robotic arm 116 (e.g., the robotic arm 116 must move at a slower speed, the robotic arm 116 must be performing surgery or a surgical procedure on the anatomical element within the 3D volume, etc.). The robotic arm 116 may be controlled by the computing device 102, the navigation system 118, and/or by another component of the system 100 to avoid passing into, through, or near the first 3D volume 212 and/or the second 3D volume 216. In some embodiments, the location of the first 3D volume 212 and/or the second 3D volume 216 may be known to the computing device 102 and/or the navigation system 118, with the locations being used or taken into account when plotting one or more navigation paths for the robotic arm 116. For example, the computing device 102 may know the pose (e.g., position and/or orientation) of the first 3D volume 212, and may use this pose information along with pose information of the robotic arm 116 to determine a navigation path for the robotic arm 116 such that the robotic arm 116 (and/or components thereof such as end effector, joints, surgical tools coupled to the end effector, etc.) avoids contacting, passing through, entering into, or otherwise interacting with the first 3D volume 212. Examples of components and/or surgical tools that may be coupled or connected to the robotic arm 116 may include a surgical drill, a surgical saw, a surgical scalpel, a surgical reamer, a surgical tap, an ultrasonic blade, a surgical burr, a screw (e.g., a surgical screw), a surgical rod, an interbody element (e.g., an interbody cage, a clamp, a spacer, etc.), combinations thereof, and/or the like. However, the components that can be connected to the robotic arm 116 are in no way limited to the foregoing list, and additional or alternative instruments, components, objects, or elements may be affixed to, attached to, or otherwise coupled with the robotic arm 116.

The first 3D volume 212 and/or the second 3D volume 216 may be defined based on registration data. The registration data may include information relating to the registration of the robotic arm 116 with the first anatomical element 204; the second anatomical element 208; other anatomical elements; surgical objects (e.g., surgical tools, patient bed, etc.); combinations thereof; and/or the like. In some embodiments, the registration data may be or comprise information related to registrations based on preoperative imaging. For instance, one or more preoperative images (e.g., CT scans, X-rays, fluoroscopic images, MRIs, etc.) may be captured using, for example, imaging devices 112. The one or more preoperative images may be processed (e.g., using image processing 120) and the processed image data may be used to register the robotic arm 116 to the first anatomical element 204 and/or the second anatomical element 208. In some embodiments, the registration 128 may map coordinates associated with each of the first anatomical element 204, second anatomical element 208, and robotic arm 116 into a common coordinate space (e.g., a patient coordinate space).

As illustrated in FIG. 2B, more than one robotic arm may be present or used for a surgery or surgical procedure. For instance, a first robotic arm 220A and a second robotic arm 220B may be use or otherwise be present. Notwithstanding the foregoing, additional or alternative robotic arms to the first robotic arm 220A and the second robotic arm 220B may be included or used in the surgery or surgical procedure.

The first robotic arm 220A and the second robotic arm 220B may be similar to or the same as the robotic arm 116, and each robotic arm may respectively include a first end effector 224A and a second end effector 224B. In some embodiments, the first robotic arm 220A and the second robotic arm 220B may be used during a surgery or surgical procedure, which may include surgical operations on or near the first anatomical element 204, the second anatomical element 208, a third anatomical element 236, and a fourth anatomical element 244. It is to be understood that, notwithstanding the foregoing, additional or alternative anatomical elements may be present, subject to the surgery or surgical procedure, or otherwise identified by the system 100 (e.g., using image data captured by the imaging devices 112). The first anatomical element 204, the second anatomical element 208, the third anatomical element 236, and/or the fourth anatomical element 244 may be or comprise vertebrae (e.g., vertebrae of the spine), with one or more of the vertebrae designated to undergo a surgery or surgical procedure. For example, a spinal fusion may be performed on two of the vertebrae, while the remainder of the vertebrae are not intended to be part of the surgery or surgical procedure. In such embodiments, the vertebrae not intended to be part of the surgery or surgical procedure, but nonetheless located within the working volume or surgical site, may include 3D volumes defined therearound (e.g., by the computing device 102, the navigation system 118, etc.), such that the robotic arm 116, when caused to move by the computing device 102 and/or the navigation system 118, does not move near, through, or within the 3D volumes. In other embodiments, components of the system 100 may move within or through the 3D volumes. Additionally or alternatively, the 3D volumes may be used by the computing device 102 to design and/or plan navigation routes or paths for the robotic arm 116 such that the robotic arm 116 passes through the 3D volumes. In other words, the computing device 102 may take into consideration the pose of one or more of the 3D volumes when plotting the movements of the robotic arm 116. During or after designing the navigation path, the computing device 102 may indicate to the navigation system 118 that the robotic arm 116 will pass through one or more of the 3D volumes, and the navigation system 118 may control the robotic arm 116 such that the robotic arm 116 moves, for example, more slowly through the 3D volume. Such alternation of movement of the robotic arm 116 may reduce the risk of the robotic arm 116 inadvertently or accidently contacting, for example, patient anatomy when moving through the 3D volume.

Each of the first anatomical element 204, the second anatomical element 208, the third anatomical element 236, and the fourth anatomical element 240 may include a respective 3D volume. In some embodiments, one or more of the 3D volumes may include one or more sub-volumes or sub-sections therein. Additionally or alternatively, one or more of the 3D volumes may be broken into separate 3D volumes that cover subsections or components of one or more anatomical elements, as discussed in greater detail below.

The first anatomical element 204 may include a first 3D volume 212 and a second 3D volume 216. The first 3D volume 212 and the second 3D volume 216 may indicate volumes through which the first robotic arm 220A and/or the second robotic arm 220B (and/or components attached thereto such as the first end effector 224A and/or the second end effector 224B) may not pass. In some embodiments, the first 3D volume 212 may encompass a first portion 204A of the first anatomical element 204 while the second 3D volume 216 may include a second portion 204B of the first anatomical element 204. In some embodiments, the first portion 204A and the second portion 204B may be portions of the first anatomical element 204 that are not subject to the instant surgery or surgical procedure, and thus may be identified (e.g., by the computing device 102, by the navigation system 118, etc.) as areas that should be avoided by the first robotic arm 220A and/or the second robotic arm 220B. In some embodiments, the first anatomical element 204 may include a third portion 204C upon which a surgery or surgical procedure is to be performed. In these embodiments, a 3D volume may not encompass the third portion 204C, permitting the first robotic arm 220A and/or the second robotic arm 220B to access the third portion 204C.

The second anatomical element 208 may include a third 3D volume 228. The third 3D volume 228 may encompass the entirety of the second anatomical element 208. In some embodiments, the encapsulation of the second anatomical element 208 by the third 3D volume 228 may indicate that the second anatomical element 208 may not be a relevant anatomical element for the surgery or surgical procedure (e.g., a vertebra that is not subject to a spinal fusion operation). As such, the third 3D volume 228 should not be entered, passed or navigated through, or otherwise interacted with by the first robotic arm 220A and/or the second robotic arm 220B (and/or components thereof). The definition of the third 3D volume 228 around the second anatomical element 208 (e.g., by the computing device 102) may cause the navigation system 118 to use navigation paths for the first robotic arm 220A and/or the second robotic arm 220B that avoid the third 3D volume 228, reducing the probability that the first robotic arm 220A and/or the second robotic arm 220B accidently contact the third 3D volume 228.

In some embodiments, the third 3D volume 228 may abut one or more of the first 3D volume 212 and the second 3D volume 216. As depicted in FIG. 2B, the third 3D volume 228 may abut the second 3D volume 216, such that there is no volume between the second 3D volume 216 and the third 3D volume 228. In some embodiments, the third 3D volume 228 (or, more generally, any of the other 3D volumes) may encompass more than one anatomical element (e.g., the third 3D volume 228 may encompass portions of the first anatomical element 204 and portions of the second anatomical element 208).

In other embodiments, the third 3D volume 228 may include a 3D sub-volume 232. The 3D sub-volume 232 may provide an additional layer of security around the second anatomical element 208. In some embodiments, the third 3D volume 228 may be defined by the computing device 102 and/or the navigation system 118 such that the first robotic arm 220A and/or the second robotic arm 220B may pass into the third 3D volume 228, but not the 3D sub-volume 232. In such embodiments, the passing of the first robotic arm 220A and/or the second robotic arm 220B (and/or components thereof) into the volume inside the third 3D volume 228 but outside the 3D sub-volume 232 may result in the movements and/or operations first robotic arm 220A and/or the second robotic arm 220B (and/or components thereof) being altered. For example, a first end effector 224A of the first robotic arm 220A may include a surgical tool that is powered off when the first end effector 224A enters the third 3D volume 228. Additionally or alternatively, the movement of the first robotic arm 220A (and, by extension, the first end effector 224A) may be stopped or otherwise halted upon entering the third 3D volume 228. In other words, the third 3D volume 228 may operate as a buffer zone between the first robotic arm 220A and/or the second robotic arm 220B and the 3D sub-volume 232 (and by extension the second anatomical element 208), where the navigation, operation, and/or movement of the first robotic arm 220A and/or the second robotic arm 220B is altered when passing into the third 3D volume 228.

The third anatomical element 236 may include a fourth 3D volume 240 and the fourth anatomical element 244 may include a fifth 3D volume 248. The fifth 3D volume 248 may encompass a first portion 244A of the fourth anatomical element 244, while a second portion 244B of the fourth anatomical element 244 may be omitted from the fifth 3D volume 248. The fourth 3D volume 240 and the fifth 3D volume 248 may include an overlap 252. In such embodiments, the overlap 252 may be high-risk volume, or otherwise a volume where there is an increased chance of unintentional contact between the first robotic arm 220A and/or the second robotic arm 220B (and/or components thereof) and the third anatomical element 236 and/or the fourth anatomical element 244. The computing device 102 may construct navigation paths for the first robotic arm 220A and/or the second robotic arm 220B and, when the first robotic arm 220A and/or the second robotic arm 220B crosses into the overlap 252, the operation, movement, and/or navigation of the first robotic arm 220A and/or the second robotic arm 220B may be altered. For example, if the first robotic arm 220A crosses into the overlap 252 (whether accidentally, due to imprecise navigation path construction, or for any other reason), the computing device 102 may stop the movement of the first robotic arm 220A, may power down or turn off any surgical tools associated with the first robotic arm 220A (e.g., turning off a surgical drill mechanically coupled with the first robotic arm 220A), and/or adjust the navigation path of the first robotic arm 220A such that the first robotic arm 220A exits the overlap 252.

In some embodiments, the 3D volumes may be spaced apart or otherwise physical separated. For instance, the third 3D volume 228 and the fourth 3D volume 240 may be separated by a first distance 256. In some embodiments, the volume between the third 3D volume 228 and the fourth 3D volume 240 may be an unrestricted zone, such that the first robotic arm 220A and/or the second robotic arm 220B may pass through the volume.

Figure 3:
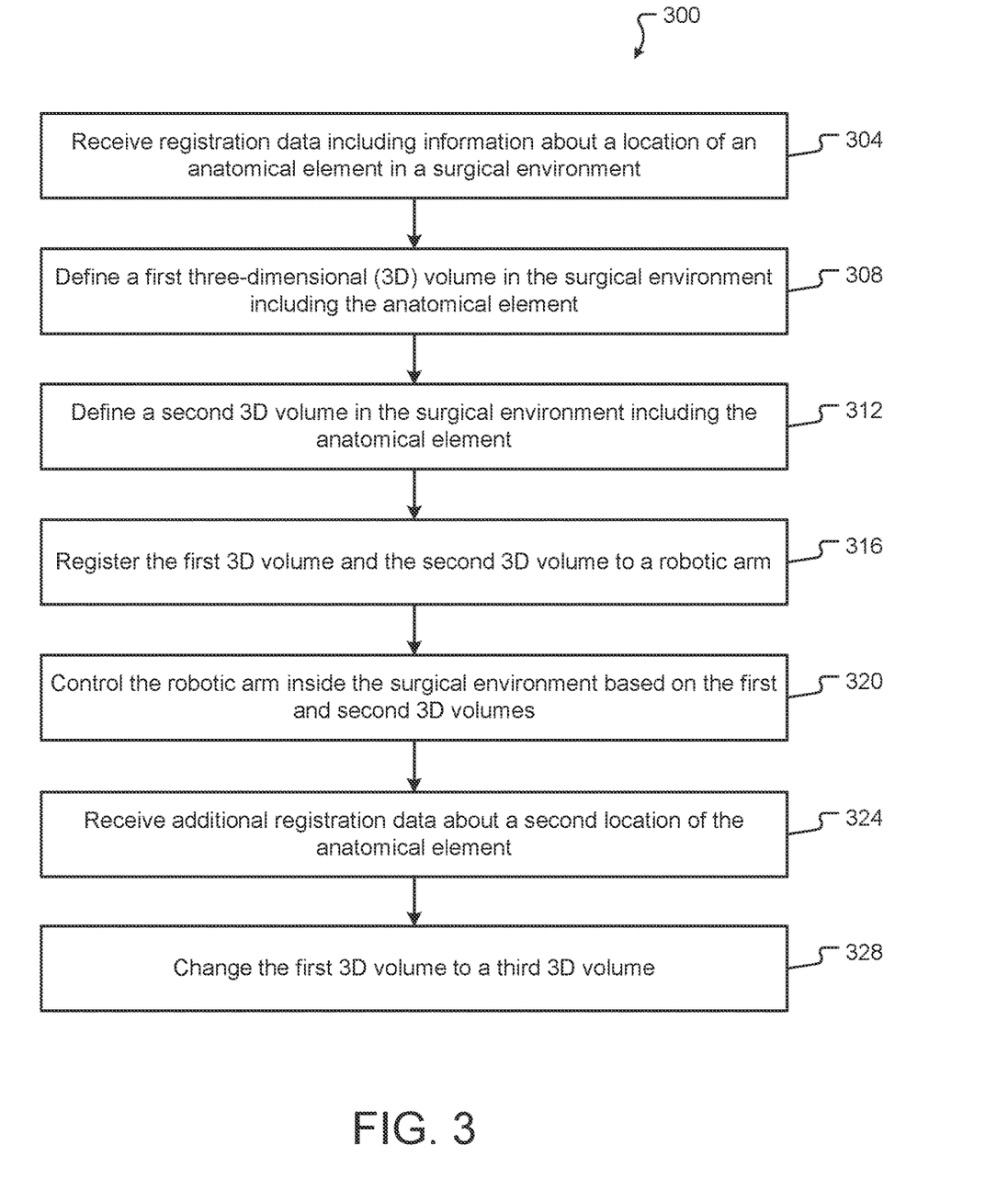
FIG. 3 is a flowchart according to at least one embodiment of the present disclosure.

FIG. 3 depicts a method 300 that may be used, for example, do define one or more 3D volumes around one or more anatomical elements.

The method 300 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 300. The at least one processor may perform the method 300 by executing elements stored in a memory such as the memory 106. The elements stored in memory and executed by the processor may cause the processor to execute one or more steps of a function as shown in method 300. One or more portions of a method 300 may be performed by the processor executing any of the contents of memory, such as an image processing 120, a segmentation 122, a transformation 124, and/or a registration 128.

The method 300 comprises receiving registration data including information about a location of an anatomical element in a surgical environment (step 304). The surgical environment may include the one or more anatomical elements, the robotic arm, other patient anatomy (up to and including the patient), a navigation system (e.g., navigation system 118), combinations thereof, and/or the like. In some embodiments, the surgical environment may be or comprise a working volume that is a 3D space subject to the surgery or surgical procedure.

The registration data may be or comprise information related to the registration of a robotic arm (e.g., a robotic arm 116, a first robotic arm 220A, a second robotic arm 220B, etc.) and/or one or more components thereof (e.g., first end effector 224A, a second end effector 224B, etc.) to one or more anatomical elements (e.g., a first anatomical element

204, a second anatomical element 208, a third anatomical element 236, a fourth anatomical element 244, etc.), or vice versa. For example, the registration data may contain coordinates of the robotic arm and/or the anatomical element(s) in one or more coordinate spaces (e.g., a patient coordinate space, a coordinate space for an anatomical element, a coordinate space for a robotic arm, etc.). The information about the location of the anatomical element may be or comprise the location of anatomical element relative to the robotic arm and/or to another element in a shared coordinate space. In other words, the information may enable a computing device 102, a navigation system 118, combinations thereof, and/or the like do determine the position of the anatomical element relative to the robotic arm and, based on the position, determine a possible navigation path of the robotic arm to avoid unintentionally contacting the anatomical element.

The method 300 also comprises defining a first 3D volume in the surgical environment including the anatomical element (step 308). The step 308 may utilize or implement transformations (e.g., transformations 124) that receive location information about the anatomical element (e.g., a plurality of coordinate points in a coordinate space) and define the first 3D volume therearound. The volume may be determined based on the tolerances of the transformations 124, the type of surgery or surgical procedure, the size or pose of the anatomical element, combinations thereof, and/or the like. For example, in surgeries or surgical procedures with sensitive anatomical elements (e.g., anatomical elements such as arteries and/or nerves that, if disturbed, may result in patient harm, discomfort, and/or pain), the 3D volumes may encompass a greater volume around the anatomical element than in embodiments where the anatomical elements are less sensitive (e.g., when the anatomical comprises bone or other hard tissues). In some embodiments, the transformations may be or comprise machine learning and/or artificial intelligence models trained on historical image data that can define the first 3D volume around the anatomical element. For example, the model may be trained on data associated with similar surgical procedures, such that the model can determine an acceptable (e.g., with a certain degree of statistical certainty) 3D volume such that by avoiding the 3D volume, the robotic arm is unlikely (within a degree of statistical certainty) to contact the anatomical element.

In some embodiments, the first 3D volume may encompass a first portion of the anatomical element. For example, the anatomical element may comprise a vertebra that includes a first portion, a second portion, and a third portion, with the first and second portions of the vertebra not being subject to the surgery or surgical procedure. In such embodiments, the third portion of the vertebra may be subject to the surgery or surgical procedure and may physically separate the first portion and the second portion of the vertebra. As such, the computing device 102 may define 3D volumes around the first portion and the second portion, but not the third portion, of the vertebra to enable the robotic arm to access the third portion while also avoiding the first and second portions.

In some embodiments, first 3D volume may be defined to encompass multiple anatomical elements. For example, the multiple anatomical elements may comprise a plurality of vertebrae not subject to an instant surgery or surgical procedure, and thus may encompassed by the first 3D volume. The encompassing of multiple elements by a single 3D volume (rather than, for example, single 3D volumes for each vertebrae in the plurality of vertebrae) may be used by the navigation system to construct navigation paths that avoid the single 3D volume, rather than considering the multiple 3D volumes in constructing the navigation path of the robotic arm. Notwithstanding the foregoing, in some embodiments the system may designate a plurality of 3D volumes for a plurality of vertebrae, and use each 3D volume in the plurality of 3D volumes in planning a navigation path.

The method 300 also comprises defining a second 3D volume in the surgical environment including the anatomical element (step 312). In some embodiments, the step 312 may be similar to or the same as the step 308. For instance, the step 312 may use one or more transformations to define the second 3D volume. The second 3D volume may encompass the second portion of the anatomical element. As previously discussed, the anatomical element may be or comprise a vertebra have multiple portions, with some portions designated as being operated on during a surgery or surgical procedure, while other portions are not subject to the surgery or surgical procedure. As such, the second 3D volume may encompass the second portion of the vertebra, such that navigation routes by a robotic arm avoid passing into or through the second 3D volume.

The method 300 also comprises registering the first 3D volume and the second 3D volume to a robotic arm (step 316). The step 316 may utilize or implement one or more registrations (e.g., registrations 128) to register the first 3D volume and the second 3D volume to the robotic arm. The registrations may implement one or more algorithms or mathematical operations to map coordinates associated with each of the first and second 3D volumes into a coordinate space associated with the robotic arm, map coordinates associated with the robotic arm into either of the coordinate spaces associated with the first and second 3D volumes, or map coordinates associated with the robotic arm and coordinates associated with the first and second 3D volumes into a shared or other coordinate space (e.g., a patient coordinate space). In some embodiments, such registration may be passed to one or more components of the system 100 (e.g., the computing device 102, the navigation system 118, etc.).

The method 300 also comprises controlling the robotic arm inside the surgical environment based on the first and second 3D volumes (step 320). The controlling may include moving the robotic arm inside the surgical environment (e.g., a working volume), such that the robotic arm avoids passing through or into the first 3D volume and/or the second 3D volume. In some embodiments, the robotic arm may be controlled to pass through the first 3D volume and/or the second 3D volume, but with modified movement. For example, the robotic arm may pass through the 3D volumes, but at reduced speeds. As another example, the robotic arm may pass through the 3D volumes, but only if the robotic arm is not mechanically coupled with a surgical tool (e.g., a drill).

The method 300 also comprises receiving additional registration data about a second location of the anatomical element (step 324). The additional registration data may be or comprise information based on one or more intraoperative images (e.g., images captured during the course of a surgery or surgical procedure). The additional registration data may be used to update, alter, or replace the registration data received in the step 304, or may be otherwise combined with the original registration data. The additional registration data may comprise information pertaining to locations of one or more anatomical elements, including the anatomical element around which the first 3D volume and the second 3D volume have been defined. In some embodiments, the locations may reflect a change in pose of the anatomical element. For example, the anatomical element may have shifted in a first direction (e.g., due to movement caused by vibrations generated by a surgical tool operating on an anatomical element, due to movement of the patient during the surgery or surgical procedure, etc.). Due to the shift, the first 3D volume may no longer fully encompass the first portion of the anatomical element (e.g., coordinates associated with the first portion no longer fall within the boundaries defined by the first 3D volume), and the anatomical element may now be positioned in the second location.

The method 300 also comprises changing the first 3D volume to a third 3D volume (step 328). The third 3D volume may be an expansion, contraction, pose change, or any other change to the first 3D volume. Continuing the above example, the shift of the anatomical element in the first direction may result in the first 3D volume no longer fully encompassing the first portion of the anatomical element. The step 328 may use or implement one or more transformations (e.g., transformations 124) that determine the shift of the anatomical element (e.g., based off one or more preoperative images processed by image processing 120 to determine coordinates associated with the new position of the anatomical element) and change the first 3D volume to the third 3D volume. In some embodiments, the third 3D volume may be a volumetric expansion of the first 3D volume in the first direction, such that the anatomical element is once again encompassed by the third 3D volume. In other embodiments, the volume of the first 3D volume and the third 3D volume may be similar or the same but with a different pose. For example, the third 3D volume may be the same as the first 3D volume but shifted in the first direction. In other words, the volume may remain constant, but the pose of the first 3D volume is changed to match the change in pose of the anatomical element.

The present disclosure encompasses embodiments of the method 300 that comprise more or fewer steps than those described above, and/or one or more steps that are different than the steps described above.

Figure 4:
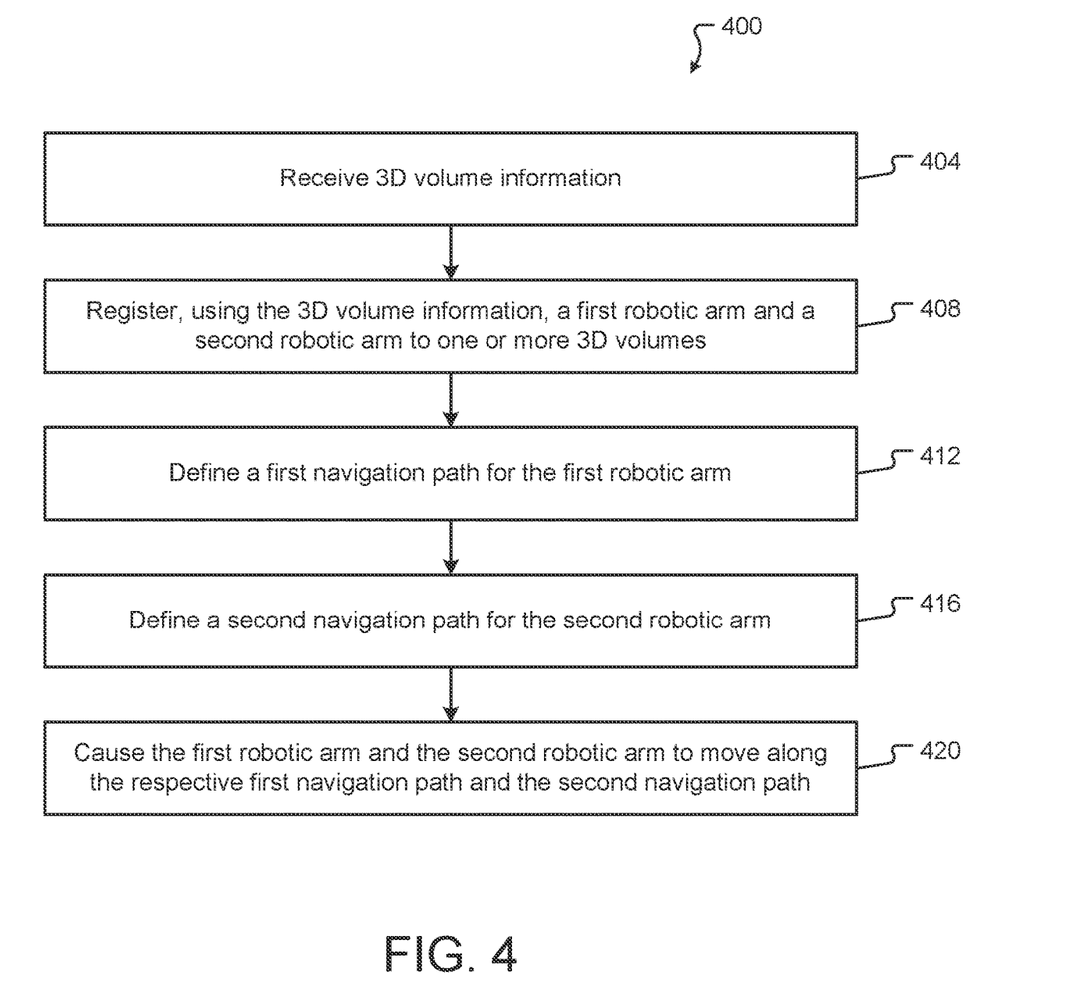
FIG. 4 is a flowchart according to at least one embodiment of the present disclosure.

FIG. 4 depicts a method 400 that may be used, for example, to navigate one or more robotic arms based on defined 3D volumes.

The method 400 (and/or one or more steps thereof) may be carried out or otherwise performed, for example, by at least one processor. The at least one processor may be the same as or similar to the processor(s) 104 of the computing device 102 described above. The at least one processor may be part of a robot (such as a robot 114) or part of a navigation system (such as a navigation system 118). A processor other than any processor described herein may also be used to execute the method 400. The at least one processor may perform the method 400 by executing elements stored in a memory such as the memory 106. The elements stored in memory and executed by the processor may cause the processor to execute one or more steps of a function as shown in method 400. One or more portions of a method 400 may be performed by the processor executing any of the contents of memory, such as an image processing 120, a segmentation 122, a transformation 124, and/or a registration 128.

The method 400 comprises receiving 3D volume information (step 404). The 3D volume information may be or comprise locations of one or more 3D volumes encompassing anatomical elements (and/or components thereof). For instance, the 3D volume information may include coordinate values for each of the one or more 3D volumes in one or more coordinate spaces. Additionally or alternatively, the 3D volume information may be or comprise information related to coordinate values within the 3D volumes. Such information may be useful, for example, in defining one or more navigation paths along which a robotic arm can navigate. Such coordinates may be off limits to the robotic arm (e.g., the robotic arm cannot occupy such coordinates because they reside inside the 3D volume), and the computing device 102 and/or navigation system 118 may be able to verify the navigation path by predicting coordinates occupied by the robotic arm and, when such predictions occupy the 3D volume, adjust the navigation route such that the robotic arm avoids the 3D volume.

The method 400 also comprises registering, using the 3D volume information, a first robotic arm and a second robotic arm to one or more 3D volumes (step 408). The step 408 may utilize or implement one or more registrations (e.g., registrations 128) that use the 3D volume information and robotic arm pose information of each of the robotic arms to determine the locations of the robotic arms relative to the 3D volumes. For example, the registration 128 may receive coordinate information associated with each of the one or more 3D volumes (e.g., vertex coordinates of each of the 3D volumes, boundary coordinates of each of the 3D volumes, combinations thereof, and/or the like) as well as pose information for each robotic arm (e.g., coordinates associated with each robotic arm in a coordinate space) to map the coordinates of each of the 3D volumes and of each robotic arm into a common coordinate space (e.g., a patient coordinate space). Additionally or alternatively, the 3D volume information may include coordinates of each of the one or more anatomical elements contained wholly or partially within one or more of the 3D volumes, with such coordinates being mapped to the common coordinate space.

The method 400 also comprises defining a first navigation path for the first robotic arm (step 412). The step 412 may utilize or implement one or more transformations 124 that determine a first navigation path for the first robotic arm. The transformations 124 may be machine learning or artificial intelligence models trained on surgical and/or historical data to determine the first navigation path. The models may take the pose information of the first robotic arm, location information of the one or more 3D volumes, and/or information from the surgical plan (e.g., type of surgery or surgical procedure) as inputs and output the first navigation path. The first navigation path may cause the first robotic arm to avoid the one or more 3D volumes (e.g., the first robotic arm does not pass through the one or more 3D volumes, the first robotic arm avoids passing through the one or more 3D volumes, etc.).

The method 400 also comprises defining a second navigation path for the second robotic arm (step 416). In some embodiments, the defining of the second navigation path may be similar to or the same as the defining of the first navigation path in the step 412. In some embodiments, the defining of the second navigation path may also take into account the first navigation path determined in the step 412. For example, the step 416 may use a one or more transformations (e.g., transformations 124) that take the first navigation path, pose information of the second robotic arm, location information of the one or more 3D volumes, and/or information from the surgical plan (e.g., type of surgery or surgical procedure) to determine the second navigation path. In some embodiments, the incorporation of the first navigation path may ensure that the second robotic arm does not collide with the first robotic arm during the movement of the first robotic arm along the first navigation path and the second robotic arm along the second navigation path.

The method 400 also comprises causing the first robotic arm and the second robotic arm to move along the respective first navigation path and the second navigation path (step 420). In some embodiments, a computing device (e.g., computing device 102), a navigation system (e.g., navigation system 118), and/or other controller may active one or more motors and/or engage and/or disengage one or more locks on one or more joints of the robotic arm such that the first robotic arm moves along the first navigation path, and the second robotic arm moves along the second navigation path. In some embodiments, the movement of the first robotic arm and/or the second robotic arm may be tracked based on the registration of the robotic arms to the 3D volumes by the computing device and/or the navigation system. In such embodiments, deviations from the navigation path (e.g., within a statistically significant variation) and/or any entry of the first robotic arm and/or the second robotic arm into any one or more of the 3D volumes may generate one or more alerts (e.g., an alarm, a visual warning rendered to a display, etc.), and may additionally or alternatively result in the computing device and/or the navigation system causing the navigation of the first robotic arm and/or the second robotic arm along respective first and second navigation paths to stop.

The present disclosure encompasses embodiments of the method 400 that comprise more or fewer steps than those described above, and/or one or more steps that are different than the steps described above.

As noted above, the present disclosure encompasses methods with fewer than all of the steps identified in FIGS. 3 and 4 (and the corresponding description of the methods 300 and 400), as well as methods that include additional steps beyond those identified in FIGS. 3 and 4 (and the corresponding description of the methods 300 and 400). The present disclosure also encompasses methods that comprise one or more steps from one method described herein, and one or more steps from another method described herein. Any correlation described herein may be or comprise a registration or any other correlation.

The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the foregoing has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method, comprising:
   receiving first registration data including information about a location of a first anatomical element in a surgical environment;
   receiving second registration data including information about a location of a second anatomical element in the surgical environment;
   defining, based on the location of the first anatomical element, a first three-dimensional (3D) volume in the surgical environment including a first portion of the first anatomical element;
   defining, based on the location of the second anatomical element, a second 3D volume different from the first 3D volume in the surgical environment, wherein the second 3D volume comprises a second portion of the first anatomical element different than the first portion of the first anatomical element, and wherein the second 3D volume comprises an entirety of the second anatomical element; and
   controlling a robotic arm inside the surgical environment based on the first 3D volume and the second 3D volume such that at least one of the robotic arm and one or more components attached to the robotic arm avoids passing through the first 3D volume during a movement of the robotic arm.

2. The method of claim 1, wherein the first registration data includes information from one or more of a Computed Tomography (CT) image, a Magnetic Resonance Image (MRI), and a fluoroscopic image.

3. The method of claim 1, further comprising:
   registering the first 3D volume to the robotic arm;
   defining, based on the location of the second anatomical element and a location of the second 3D volume, a first 3D sub-volume within the second 3D volume; and
   controlling the robotic arm based on the first 3D sub-volume such that at least one of the robotic arm and the one or more components attached to the robotic arm passes through the second 3D volume and avoids passing through the first 3D sub-volume.

4. The method of claim 1, wherein the first anatomical element comprises at least one of a vertebra, a hard tissue, a soft tissue, an artery, and a nerve, and wherein the second 3D volume is positioned a first distance away from the first 3D volume.

5. The method of claim 1, further comprising:
   controlling a second robotic arm based on the first 3D volume, wherein at least one of the second robotic arm and components attached to the second robotic arm passes through the first 3D volume.

6. The method of claim 5, further comprising:
   determining, based on the first 3D volume, a first navigation path of the robotic arm; and
   determining, based on at least one of the first 3D volume and the first navigation path, a second navigation path of the second robotic arm.

7. The method of claim 5, wherein the controlling of the second robotic arm further comprises:
   restricting, when the second robotic arm passes through the first 3D volume, the movement of the robotic arm.

8. The method of claim 1, wherein the one or more components of the robotic arm comprises at least one of a surgical drill, a surgical saw, a surgical scalpel, a surgical reamer, a surgical tap, an ultrasonic blade, a surgical burr, a surgical screw, and an interbody element.

9. A system, comprising:
a processor; and
a memory storing data thereon that, when executed by the processor, cause the processor to:
receive first registration data including information about a location of a first anatomical element in a surgical environment;
receive second registration data including information about a location of a second anatomical element in the surgical environment;
define, based on the location of the first anatomical element, a first three-dimensional (3D) volume in the surgical environment comprising a first portion of the first anatomical element;
define, based on the location of the second anatomical element, a second 3D volume different from the first 3D volume in the surgical environment and comprising a second portion of the first anatomical element different than the first portion of the first anatomical element, wherein the second 3D volume encompasses an entirety of the second anatomical element; and
control a robotic arm inside the surgical environment based on the first 3D volume and the second 3D volume such that at least one of the robotic arm and one or more components attached to the robotic arm avoids passing through the first 3D volume during a movement of the robotic arm.

10. The system of claim 9, wherein the first 3D volume at least partially overlaps the second 3D volume.

11. The system of claim 9, wherein the data further cause the processor to:
define, based on the location of the second anatomical element and a location of the second 3D volume, a first 3D sub-volume encompassed by the second 3D volume, wherein the robotic arm is controlled to pass through the second 3D volume, and wherein robotic arm is controlled to avoid passing through the first 3D sub-volume.

12. The system of claim 9, wherein the robotic arm comprises an end effector, and wherein the end effector is controlled to pass through a third 3D volume that abuts at least one of the first 3D volume and the second 3D volume.

13. The system of claim 9, wherein the first 3D volume and the second 3D volume are mutually exclusive.

14. The system of claim 13, wherein an end effector of the robotic arm is mechanically coupled to a first surgical tool, and wherein the first surgical tool comprises a drill, a reamer, a scalpel, a saw, a tap, an ultrasonic blade, a surgical burr, a surgical screw, or an interbody element.

15. The system of claim 9, wherein the data further cause the processor to:

define a third 3D volume that abuts at least one of the first 3D volume and the second 3D volume; and
control the movement of the robotic arm based on the third 3D volume.

16. The system of claim 9, wherein the first registration data includes information from one or more of a Computed Tomography (CT) image, a Magnetic Resonance Image (MRI), and a fluoroscopic image.

17. An apparatus, comprising:
a robotic arm that includes an end effector;
a processor; and
a memory storing data thereon that, when executed by the processor, cause the processor to:
receive first registration data including information about a location of a first anatomical element in a surgical environment;
receive second registration data including information about a location of a second anatomical element in the surgical environment;
define, based on the location of the first anatomical element, a first three-dimensional (3D) volume in a surgical environment comprising a first portion of the first anatomical element;
define, based on the location of the second anatomical element, a second 3D volume in the surgical environment that encompasses a second portion of the first anatomical element different than the first portion of the first anatomical element, wherein the second 3D volume encompasses an entirety of the second anatomical element; and
maneuver the robotic arm inside the surgical environment based on the first 3D volume and the second 3D volume such that at the end effector of the robotic arm avoids passing into the first 3D volume.

18. The apparatus of claim 17, wherein the data further cause the processor to:
receive one or more intraoperative images;
determine, based on the one or more intraoperative images, a second location of the first anatomical element in the surgical environment; and
change, based on the one or more intraoperative images, the first 3D volume to a third 3D volume.

19. The apparatus of claim 18, wherein the third 3D volume has a volume that is different than the first 3D volume.

20. The apparatus of claim 19, wherein the second registration data include a third location of the second anatomical element, and wherein the data further cause the processor to:
define a fourth 3D volume including a portion of the second anatomical element; and
maneuver the robotic arm based on the fourth 3D volume.

* * * * *